United States Patent [19]
Hirschi et al.

[11] Patent Number: 5,325,873
[45] Date of Patent: Jul. 5, 1994

[54] TUBE PLACEMENT VERIFIER SYSTEM

[75] Inventors: Richard E. Hirschi, Lebanon; James P. Karbowski, Philomath, both of Oreg.; James L. Tiefenthal, Columbus, Ohio; Ronald M. Isaac, Libertyville, Ill.

[73] Assignees: Abbott Laboratories; White's Electronics, Inc.

[21] Appl. No.: 917,259

[22] Filed: Jul. 23, 1992

[51] Int. Cl.⁵ ............................................. A61B 19/00
[52] U.S. Cl. .............................. 128/899; 128/653.1; 128/654; 324/329; 340/573
[58] Field of Search ............ 128/899, 903, 654, 653.1, 128/897; 324/207.17, 239, 207.26, 329; 340/572, 573

[56] References Cited

U.S. PATENT DOCUMENTS

| | | | |
|---|---|---|---|
| 3,557,758 | 1/1971 | Lack | 340/572 |
| 4,173,228 | 11/1979 | Van Steenwyk et al. | 128/653.1 |
| 4,222,374 | 9/1980 | Sampson et al. | 128/899 |
| 4,361,153 | 11/1982 | Slocum et al. | 128/903 |
| 4,431,005 | 2/1984 | McCormick | 128/653.1 |
| 4,441,210 | 4/1984 | Hochmair et al. | 324/207.16 |
| 4,905,698 | 10/1991 | Strohl, Jr. et al. | 128/653.1 |
| 5,005,592 | 4/1991 | Cartmell | 128/899 |
| 5,107,862 | 4/1992 | Fabian et al. | 128/899 |

FOREIGN PATENT DOCUMENTS

| | | | |
|---|---|---|---|
| 0399536 | 11/1990 | European Pat. Off. | 128/899 |
| 2635259 | 2/1990 | France | 128/899 |
| 0000030 | 1/1990 | World Int. Prop. O. | 128/899 |

*Primary Examiner*—Lee S. Cohen
*Assistant Examiner*—Brian L. Casler
*Attorney, Agent, or Firm*—Chernoff, Vilhauer, McClung & Stenzel

[57] ABSTRACT

A system for detecting the position of an object within a body of biological tissue includes a resonant circuit attached to the object and a probe including a receiver/transmitter that operates at the resonant frequency of the object. The resonant circuit rings in response to pulses transmitted from the probe thereby activating receiver circuits which control a visual display indicating the direction the probe should be moved to center it over the object. When the object is centered a second visual display provides confirmation.

23 Claims, 10 Drawing Sheets

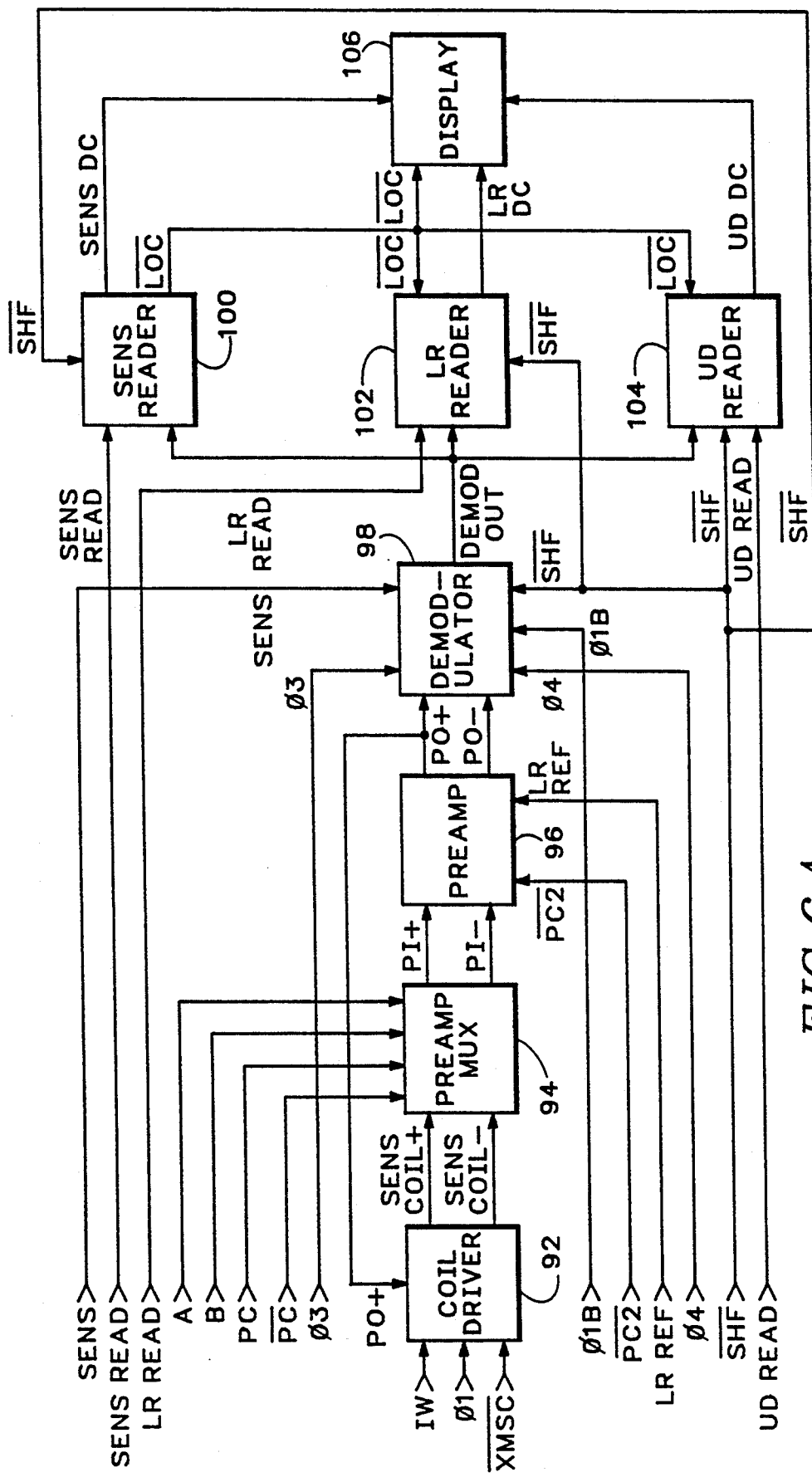

TUBE PLACEMENT VERIFIER SYSTEM

BACKGROUND OF THE INVENTION

The following invention relates to an apparatus for locating the position of an object inside a body and more particularly to a medical system for locating the position of a feeding tube inserted into the stomach of a patient to verify its position and thus prevent injury to the patient.

Enteral feeding tubes are used in certain applications with patients who are incapable of feeding themselves by conventional means. These tubes are frequently inserted through the nasal cavity and then into the stomach for nasal gastric feeding. The distal end of such tubes is perforated to allow nutrients to be delivered to the proper location once the tube has been positioned. The tubes are typically 36-45 inches in length and require proper placement within the body to insure that the nutrients will be released at the correct location and to avoid damaging any tissue. Frequently, tube placement is verified by X-ray which requires that barium sulfate or some other radio opaque material be incorporated within the tube material. Also, reference markings on the tubes are used as general guidelines for the length of tube to be inserted for nasal gastric or transpyloric tube feeding.

The verification of tube placement is critical to safe use of these devices and the methods above have not always been satisfactory for this purpose. Tube markings are themselves only a rough approximation of the actual location of the end of the tube. Using X-rays to locate the tube brings the attendant problem of harm to the patient from repeated exposure to X-rays and the expense of a radiologist to administer them.

In the past, other solutions have been proposed and an example is shown in the U.S. patent to McCormick, U.S. Pat. No. 4,431,005. In the McCormick patent a feeding tube includes a piece of metal near the distal end of the tube which is detected by a probe that generates a small local magnetic field. The field is disturbed by the magnetically permeable metal in the tube and the sensitivity of the probe can be adjusted so that an alarm indication is provided when the probe is directly adjacent the metal inside the tube. This technique takes advantage of the fact that the magnetic field is not greatly affected by the biological tissue separating the probe from the metal in the tube. A problem with the aforementioned device, however, is that it may be difficult to find the distal end of the tube with the probe. The device emits a signal only when the probe is directly over the metal in the tubing and the tiny piece of metal may be difficult to locate as the tube is being inserted into the patient. There is no direction finding feature that tells the user when the probe is in the vicinity of the metal on the end of the tube but not yet exactly centered. The system is also highly susceptible to other metal objects which may be in the vicinity such as surgical instruments, needles and the like. Metal objects are commonly used in such situations and tend to confuse a probe which is, in essence, a metal detector.

What is needed, therefore, is a position verifying device which can locate an enteral feeding tube inside body tissue with a high degree of precision so that the position of the end of the tube within the body can be known.

SUMMARY OF THE PRESENT INVENTION

The following invention provides a system for detecting the position of an object within a body or mass of material, which may be biological body tissue, and includes a resonant circuit attached to an object, such as the distal end of an enteral feeding tube, where the resonant circuit receives inductive energy of a certain frequency and rings in response thereto. Outside the body tissue a transmitter is provided for transmitting inductive energy, and a receiver is provided for detecting the ringing of the resonant circuit and providing an alarm for indicating the location of the object containing the resonant circuit inside the body tissue.

The system includes a probe positioned outside the body, and the probe may include the transmitter. The transmitter is in the form of a coil that transmits electromagnetic energy and the receiver may include pairs of coils that are wound in series opposing fashion so that the location of the resonant circuit may be determined with reference to the proximity to one or the other of the coil pairs. In this way, coil pairs that are oriented for positions which may be labeled arbitrarily "up/down" and "right/left" may be superimposed over each other to create a four quadrant pattern. Circuitry is provided that causes an alarm such as a light-emitting diode array positioned on the probe to indicate which of the four quadrants is in closest proximity to the resonant circuit. A further coil, which may be termed a sensing coil, may be provided which is a receiver coil that determines if the resonant circuit is close enough to either of the series opposed receiver coil pairs to trigger the alarm. A second LED array and associated circuitry is also provided for giving an indication of when the probe is exactly centered over the resonant circuit object.

The probe itself may be a battery powered receiver/transmitter having a substantially flat cylindrical search head in which the alarm LEDs are arranged in four quadrants on the outer peripheral surface of the cylindrical search head, and in a cluster near the center of the search head. In this way, passing the search head over the body results in an appropriate LED lighting up which indicates generally the direction of the resonant circuit object relative to the search head. Moving the search head in this direction will eventually result in the four centering LEDs lighting up which indicates that the resonant circuit object has been located and that the center of the search head, termed a "marker window," is directly over it.

The system is a pulsed system and as such the transmitter coil may also be used as the receiver sensing coil. The transmitter/sensing coil may include a pair of series aiding coils which encircle respective receiver coil pairs. The transmitter coil is pulsed to transmit energy and then it is turned off. After a dead band in the system's cycle to allow transients to die out, the receiver coils and the transmitter coil (now functioning as a sensing coil) are activated and signals on these coils are sampled over separate and discrete time windows. The signals are then demodulated and compared to determine relative amplitude and polarity. The appropriate LEDs are then activated in response to the demodulated coil signals thus indicating the location of the target.

Unambiguous and omnidirectional detection of the target is provided through the use of a target having three independent mutually orthogonal coils with appropriate capacitors to provide minimal cross coupling.

Two coils are wound in mutually orthogonal planes about a small bobbin which also houses the tiny capacitors, and a third coil is wound as a solenoid coil about the outside of the bobbin. In this way the target can be detected regardless of its spatial orientation inside the body.

Metal detection and noise resulting from the natural conductivity of biological tissue is avoided by the use of alternate transmit and receive windows with dead time provided between windows to allow most metallic target responses and signals resulting from tissue capacitance or conductivity to decay to near zero. This maximizes reception of the resonant target ringing and provides ample noise rejection.

If desired, a multiple target system may be used with resonant circuit targets having at least two differing frequencies and a search probe that can toggle between the two or more different frequencies to provide an even greater degree of directional orientation for an elongate object such as an enteral feeding tube with multiple targets attached thereto.

A principal object of this invention is to provide a system for verifying the position of an object inside a body of biological tissue or other mass with a high degree of precision.

A further object of this invention is to provide an object locating system for locating an object within a body of material which will discriminate between the object and other nearby metal objects.

A still further object of this invention is to provide a probe having the ability to search along the surface of a body or mass of material containing a resonant circuit target to find and precisely locate the position of the target.

A still further object of this invention is to provide a search head for locating an object having inherent noise rejection capability which focuses the detection circuitry on the object to be located and rejects extraneous noise.

A still further object of this invention is to provide a resonant target locator system that is a pulsed, multiplexed system that provides an improved degree of noise rejection over similar systems that operate on a continuous wave principle.

The foregoing and other objectives, features and advantages of the invention will be more readily understood upon consideration of the following detailed description of the invention, taken in conjunction with the accompanying drawings.

BRIEF DESCRIPTION OF THE DRAWINGS

FIG. 1A is a top view of a control panel located on the probe of FIG. 1.

FIG. 6A is a block schematic diagram of a continued portion of the circuits shown in FIG. 6.

DETAILED DESCRIPTION OF THE INVENTION

Figure 1:
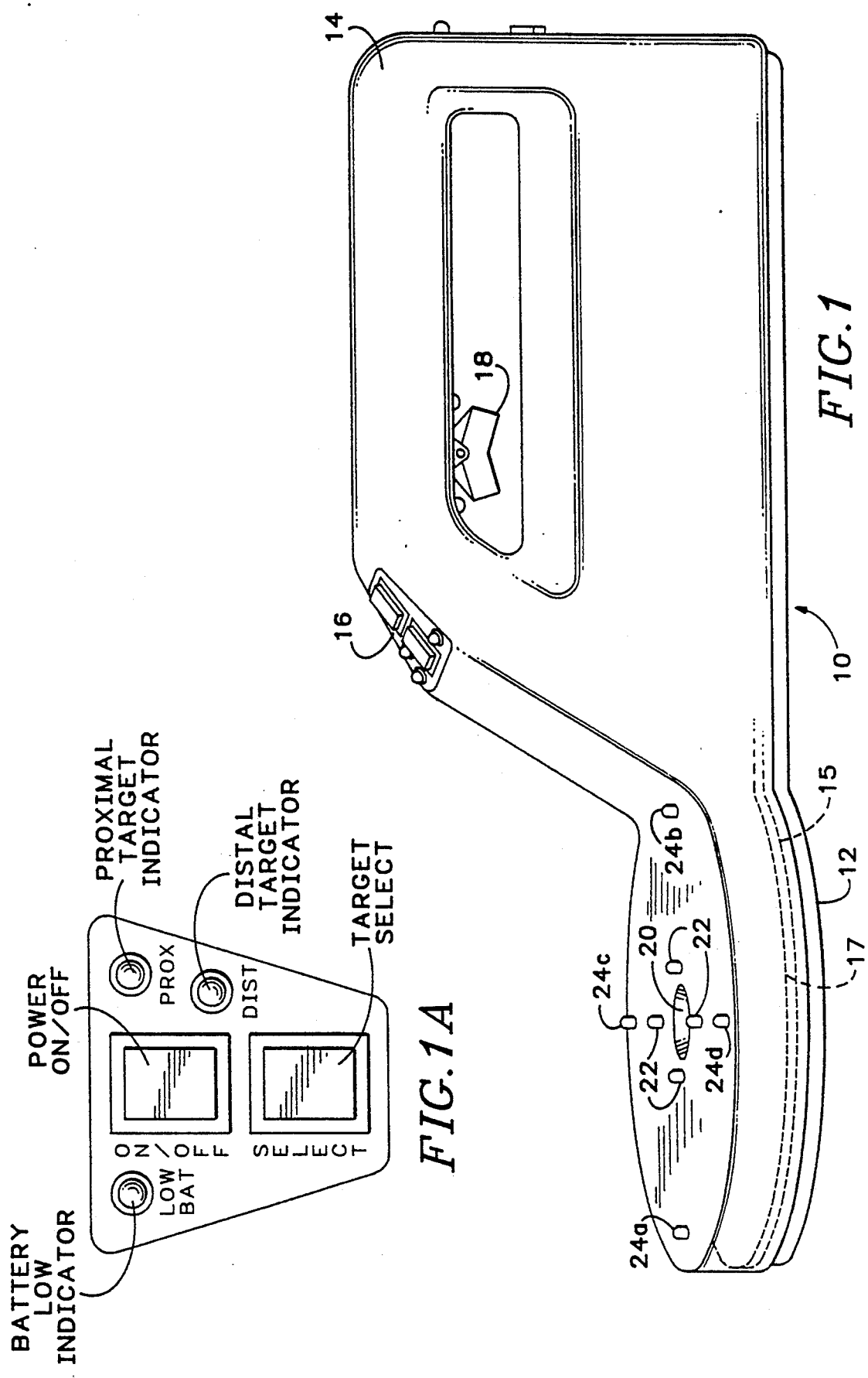
FIG. 1 is a perspective view of a probe including a search head that operates according to the present invention.

An external probe 10 includes a search head 12 and a handle portion 14. The handle portion 14 includes a control panel 16 and a .rocker switch 18. The rocker switch 18 is a search mode selector switch that has three positions. In the center position the system is constantly resetting and is not in a search mode. In the rear position the probe 10 is in a search mode as long as the switch 18 is held down, but if the switch 18 is toggled to the forward position it locks, holding the probe in a search mode until the switch is moved once again to the center position.

The search head 12 includes a center aperture 20 which serves as a target marking window. The marking window 20 is surrounded by four centering LEDs 22 which serve as pinpoint indicators to indicate that the object to be located is centered directly within the marking window 20. Directional indicators for the directions up, down, right and left, 24a, 24b, 24c and 24d, respectively, are positioned about the periphery of the search head 12. These indicators light up to indicate the direction that the search head is to be moved in order to locate the target object within the marking window 20.

Figure 2:
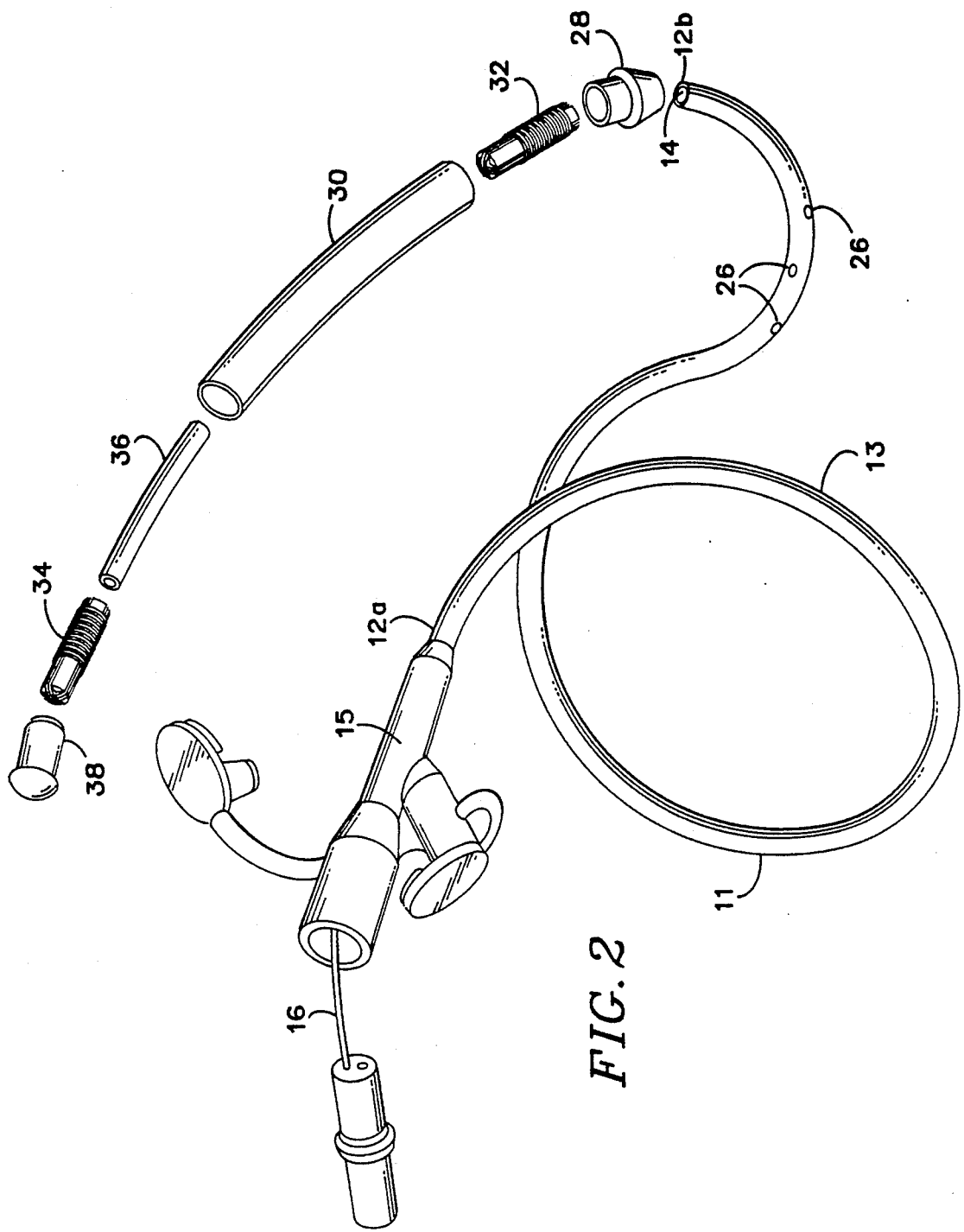
FIG. 2 is an exploded perspective view of an enteral feeding tube containing the resonant target objects to be located by the probe of FIG. 1.
Figure 2A:
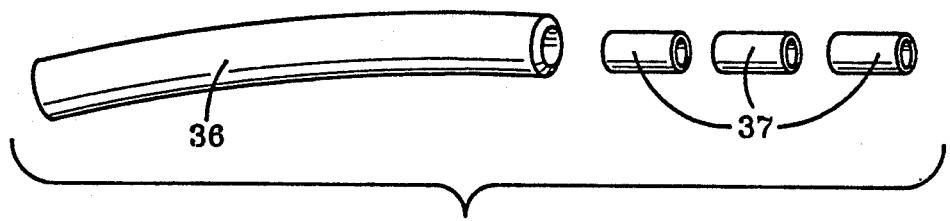
FIG. 2A is an exploded perspective view of a tubular spacing member with weights to be inserted therein.

Referring now to FIG. 2, there is shown a tube suitable for insertion into biological tissue. An enteral feeding tube 11 includes a tubular member 13 having first and second ends 12a, 12b. A longitudinally extending lumen 14 extends through the length of tubing with at least one feeding port 26 extending through a wall of the tubular member. A coupling member 28 joins the tubular member 13 to an auxiliary tubing member 30. The auxiliary tube member 30 contains two resonant circuit targets 32, 34 which are maintained in a spaced-apart relationship by a spacing member such as tubular spacing member 36. The structure and operation of the resonant circuit targets 32, 34 are described with more particularity below with reference to FIG. 5. A bolus plug 38 is attached to the auxiliary tubing member to plug the end thereof and hold the targets and tubular spacing member therein. An exploded view of the tubular spacing member 36 is presented in FIG. 2A. At least one weight 37 is disposed within the lumen of the tubular spacing member 36 for the purpose of adding weight in the vicinity of the second end 12b of the feeding tube 11, thus facilitating the placement of the tube in biological tissue. In an exemplary embodiment of the invention the number of weights is three, and the weights are comprised of tungsten. However, it is understood that any desired number of weights, of any suitable configuration and material may be used in the practice of the invention. A means for connecting the enteral feeding tube to a source of nutrition, such as a Y connector 15, may be attached to the end 12a of the tubular member 11 which is distal from the auxiliary tubing member 30. A stylet 16 may be provided for the purpose of adding rigidity to the tubular member during the process of inserting the enteral feeding tube into biological tissue. As used herein, and in the claims, an enteral feeding tube is understood to include both nasogastric and nasojejunal tubes as well as tubes which may be inserted into the digestive tract via a surgically created opening such as a gastrostomy or jejunostomy. The components of an enteral feeding tube which will contact biological tissue and/or food should be medical grade materials (such as silicone rubbers, polyurethanes and polyvinyl chloride), which have been approved by the Food and Drug Administration of the Federal Government of the United States of America for food contact and for biocompatibility. The components of the enteral feeding tube may be connected to one another using solvent bonding techniques which are suitable for the selected materials. The enteral feeding tubes of the invention may be placed using feeding tube placement techniques which are well known in the medical field.

Figure 2B:
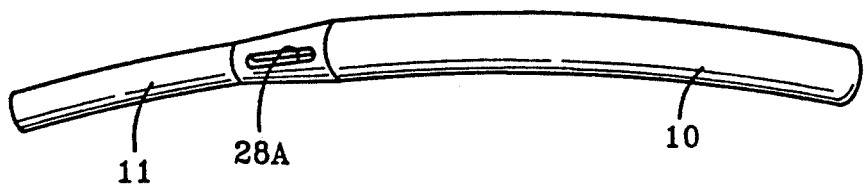
FIG. 2B is a partial perspective view of a second embodiment of an enteral feeding tube employing the invention.
Figure 2C:
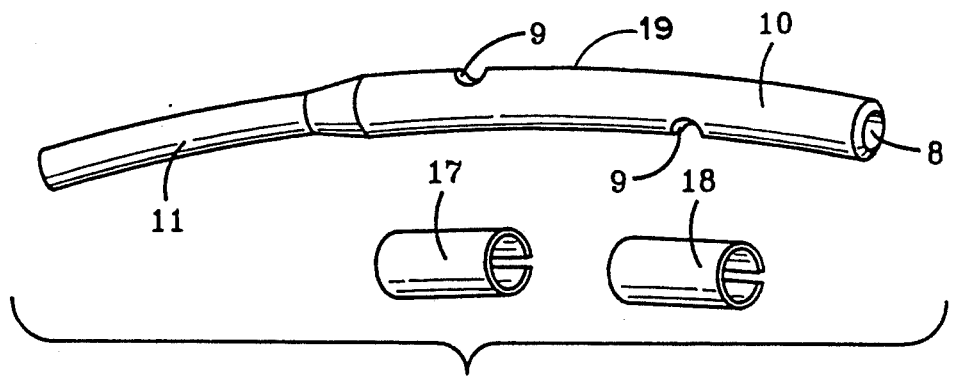
FIG. 2C is a partial exploded perspective view of an alternate embodiment of the resonant circuit targets to be affixed to an enteral feeding tube.
Figure 2D:
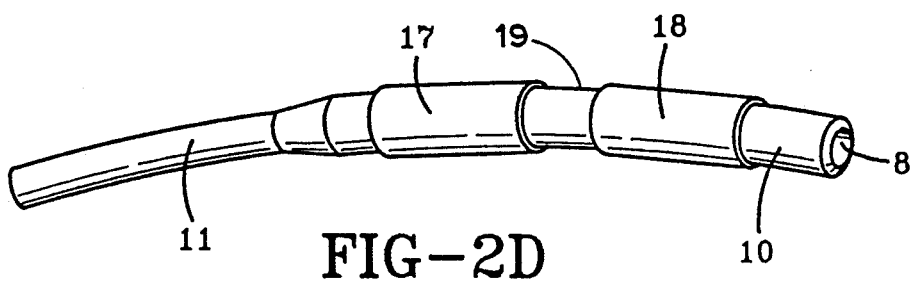
FIG. 2D is a partial perspective view of a feeding tube with resonant circuit targets attached thereto.

The structure of feeding tubes according to the present invention may be varied to accommodate the use of special materials or to incorporate other desirable features. In an alternate embodiment, as shown in FIG. 2B, the feeding ports 26 in the tubing member 11 are deleted, and the coupling member 28a which joins the tubing member to a bolus 10, has feeding ports therein. Furthermore, while the resonant circuit targets 32, 34 of the embodiment shown in FIG. 2 will not readily allow a liquid nutritional product to flow through the structure of the target, it is considered to be within the scope of the invention to employ resonant circuit targets which are tubular in structure, such as printed on a film. Such film targets 17, 18 could be placed external of a tubular member 19 as shown in FIGS. 2C and 2D. A bolus 10 could then be attached to one end of the tubular member 11, with a lumen extending through the bolus to communicate with the lumen of the tubular member and a feeding port 8 located at the end of the bolus which is distal from the tubular member. The bolus 10 may be formed of a plastic matrix having tungsten particles dispersed therein for the purpose of adding weight to facilitate placement of the feeding tube in the digestive tract. The bolus may have at least one additional feeding port 9 located along the length of the bolus as shown in FIG. 2C, or alternatively, the bolus may have a single feeding port at the end thereof as shown in FIG. 2D.

Figure 2E:
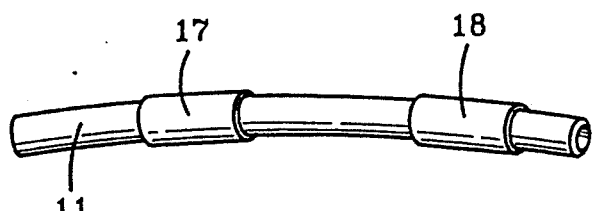
FIG. 2E is a partial perspective view of an alternate embodiment to the tube structure of FIGS. 2C and 2D.

Another alternative embodiment is presented in FIG. 2E wherein a tubular member 11 has no bolus associated therewith, but does have at least two tubular shaped resonant circuit targets 17, 18 disposed near one end thereof.

While feeding tubes have been presented as exemplary embodiments of the invention, it is understood to be within the scope of the invention to use these types of structures in other types of tubes such as tubes used in parental feeding, catheterizations, etc., which are intended for insertion into the body of a mammal.

The distal target 34 and the proximal target 32 are both resonant circuit targets and as such include coil and capacitor combinations that resonate at particular frequencies. The resonant frequency of the distal target 34 is designed to be double the resonant frequency of the proximal target 32 and the probe 10 has provision for searching at both frequencies.

Turning to FIG. 1A, the control panel for the probe includes a target select switch which toggles between the resonant frequency of the distal target 34 and that of the proximal target 32. Each target has an indicator which may be an LED labeled "prox" and "dist," respectively. The front panel also includes a power on/off switch and a low battery indicator.

Figure 3:
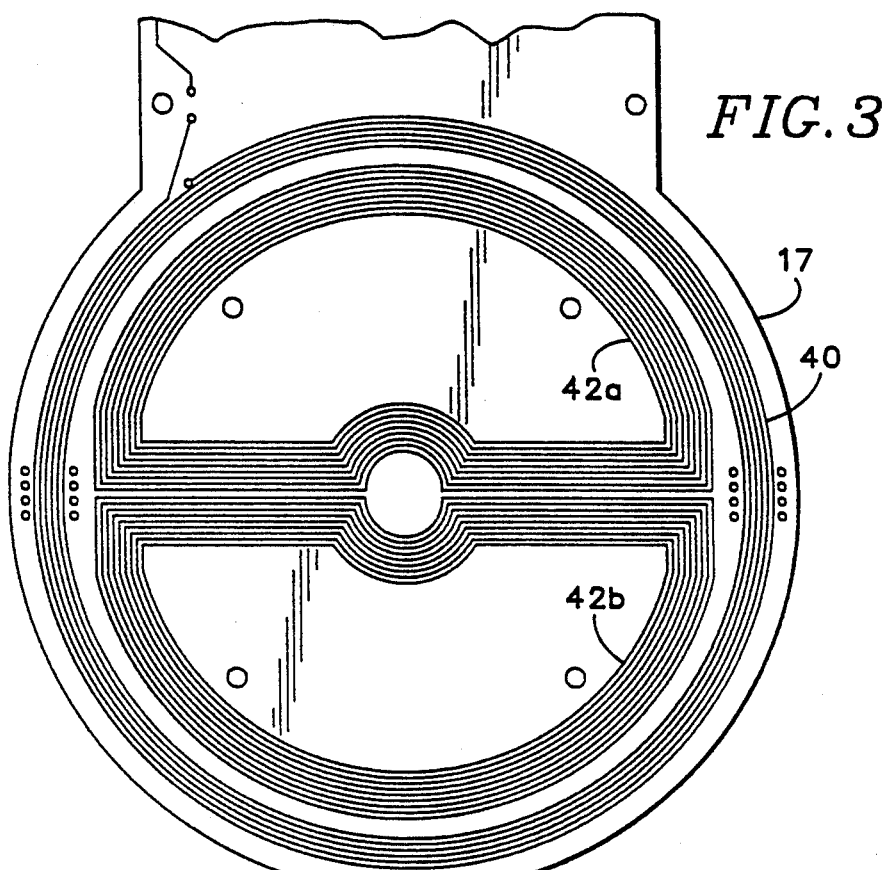
FIG. 3 is a top view of the up/down receiver coils and one of the transmitter/sensing coils located on an upper circuit board in the search head shown in the probe in FIG. 1.
Figure 4:
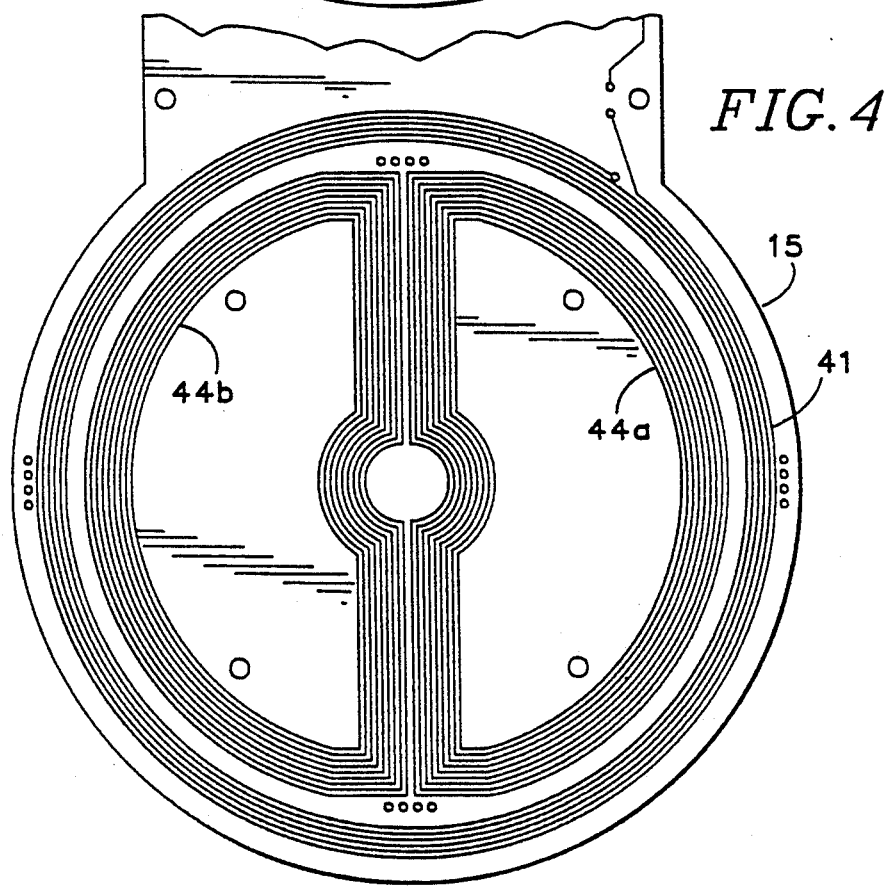
FIG. 4 is a top view of the left/right receiver coils and the other of the transmitter/sensing coils located on a bottom circuit board in the search head on the probe of FIG. 1.

The search head 12 includes a pair of parallel planar circuit boards shown in dashed outline as boards 15 and 17, respectively, that contain the transmit and receive coils shown in more detail in FIGS. 3 and 4. FIG. 3 shows the configuration of the coils on the top printed circuit board 17 which include a circular transmitter/sensing coil 40, and a pair of up/down receiver coils 42a and 42b which are positioned inside the transmitter/sensing coil 40. Each of the receiver coils 42a and 42b are D-shaped coils that are connected in series-opposed fashion. The "D" shape maximizes the use of the available area inside the sensing coil. The coils 40, 42a and 42b all lie in a common plane on the top circuit board 17. Directly underneath the board 17 is circuit board 15 which includes a second transmitter/sensing coil 41 and left/right coils 44a and 44b. The coils 44a and 44b are likewise connected in series-opposed fashion while the coils 41 and 40 are connected in series-aiding fashion. It should be noted that although boards 15 and 17 are shown as separate circuit boards, they could be considered to be the top and bottom planar surfaces of a single board.

The series opposing connection for the coils 42a, 42b, 44a and 44b is for the purpose of creating a null current condition when the target object is equidistant from the two coils. When the target lies along an axis that bisects either of the coil pairs along the flat portion of the "D" the currents generated in that coil pair will be equal and of opposite polarity, thus creating a null. If a null condition exists for both coil pairs, the target is centered. The sensing coil pair 40, 41 generates a current that determines whether the return signal strength of the target is great enough to be counted as a valid signal, thus providing inherent noise rejection by rejecting invalid targets. The series opposing connection of the coils also serves to reduce noise resulting from electromagnetic interference because for each such signal induced in one coil, an equal and opposite is induced in the other coil. Thus, sources of EMI do not have an adverse effect on the system. The series opposing connection, together with the symmetrical positioning of the transmitter coils, prevents large currents from being induced into the receiver coils.

Figure 5:
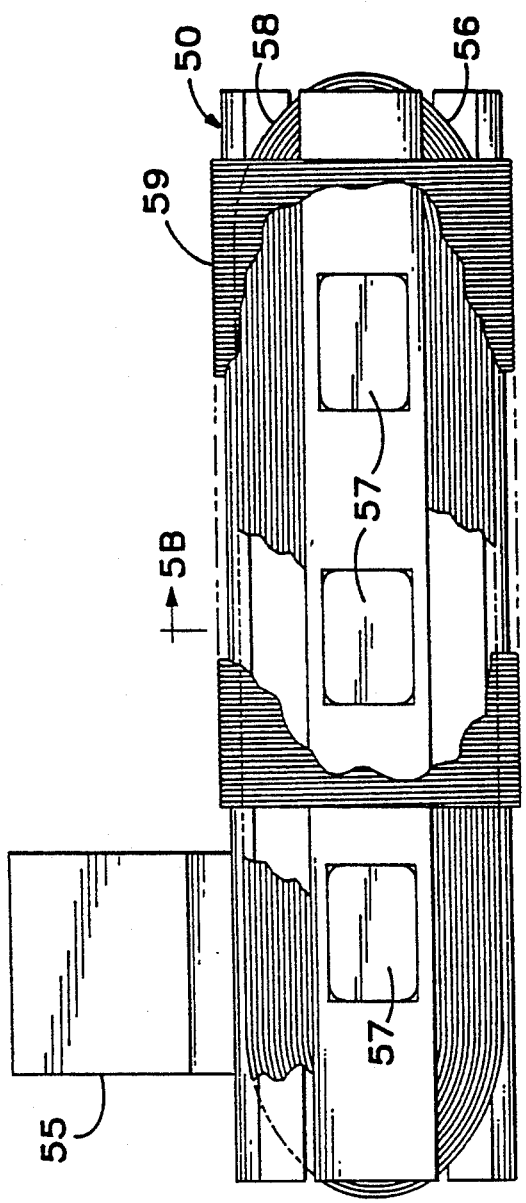
FIG. 5 is a partially cutaway side view of a resonant circuit target as used in the enteral feeding tube shown in FIG. 2.
Figure 5B:
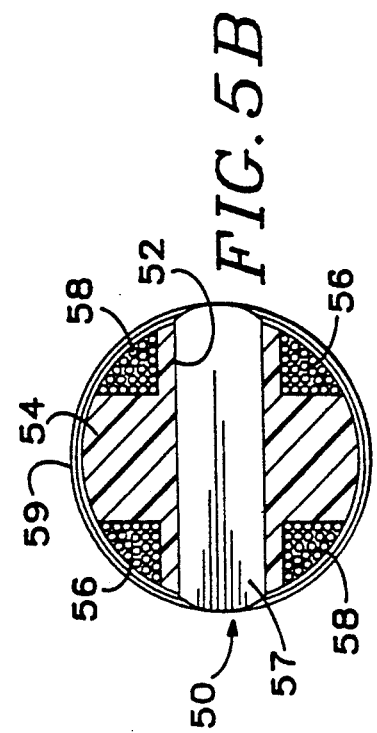
FIG. 5B is an end cutaway view taken along line 5—5 of FIG. 5.
Figure 5A:
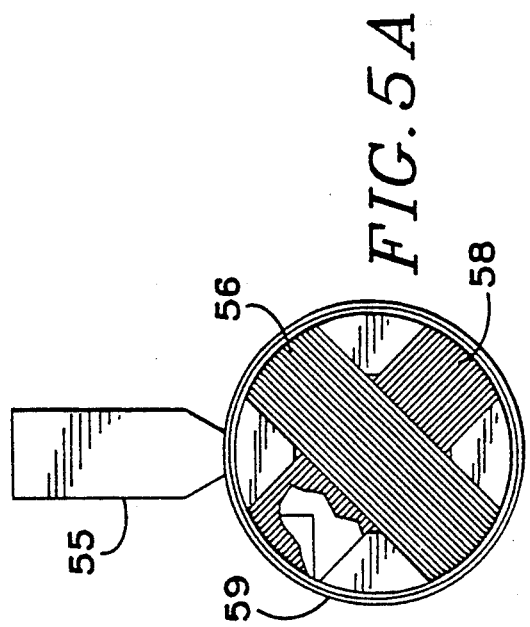
FIG. 5A is an end view, partially cutaway, of the resonant circuit target of FIG. 5.

The target object to be used with the tube placement verifier system is shown in FIGS. 5, 5a and 5b. Each target, whether it is the distal target 34 or the proximal target 32 in the system, is a multicoiled target which includes a bobbin 50 formed by a pair of mutually perpendicular cross pieces 52 and 54 (refer to FIG. 5b). A pair of mutually perpendicular coils 56 and 58 are wound lengthwise around the intersections of the cross pieces 52 and 54. A third coil 59 is wound as a solenoid coil having as its central axis the longitudinal axis of the bobbin 50. Each of the coils have capacitors 57 which are held within the body of the bobbin 50. During manufacture the bobbin 50 includes a projecting member 55 which is used to hold the bobbin in a fixture (not shown) where it can be wound. Once the bobbin has been wound, the projecting member 55 can be broken off.

The three resonant circuits thus formed (each of the coils is connected to one of the capacitors 57) have substantially identical response characteristics. Since the coils 58, 56 and 59 are mutually orthogonal in three dimensions, there is little or no cross coupling between the adjacent resonant circuits regardless of the orientation of the bolus tube 30 where the targets are housed. At any given time, at least one of the resonant circuit coils is likely to be in a plane that permits close coupling between the resonant circuit and the coils in the search head 12.

Although the solenoid coil 59 is different in configuration from the two other coils 58 and 56, it provides ample response for the probe 10 if its central axis is pointed toward the planes of the receiver coils on circuit boards 15 and 17.

Although coil 59 is a solenoid and has less area, it does have more turns than coils 58 and 56. If the wire gauge is properly selected, the resistance may be made approximately the same along with the Q and the inductance. In such a case the current induced from the solenoid coil 59 into the receiver and sensing coils turns out to be nearly the same as for coils 56 and 58 because of the higher number of turns.

Three coils on the bobbin 50 are necessary since position ambiguity may result when any single or double axis coil is positioned at an angle greater than about $22\frac{1}{2}°$ away from the plane of the search head 12 The three coil system solves this problem by providing at least one coil that will respond to the search head regardless of the position of the bolus tube 30 inside biological tissue.

Although only a single target is shown in FIGS. 5, 5a and 5b, both of the targets 34 and 32 are constructed in similar fashion with the resonant frequencies of each of the three coils on the target being the only difference. In the preferred embodiment one target has a frequency that is double the resonant frequency of the other target. For all practical purposes the 2:1 resonant frequency ratio insures that the distal target will not be picked up by the search head when the proximal target is selected for identification and vice-versa. The 2:1 frequency ratio gives better rejection because the synchronous demodulator, as will be explained below, rejects any even harmonics or subharmonics generated by the resonant targets. The use of two targets provides the search head 12 with the means of detecting the alignment of the feeding tube 11 because the relative locations of the two targets define a straight line and thus provides some indication of the alignment of at least the distal end of the tube.

Figure 6:
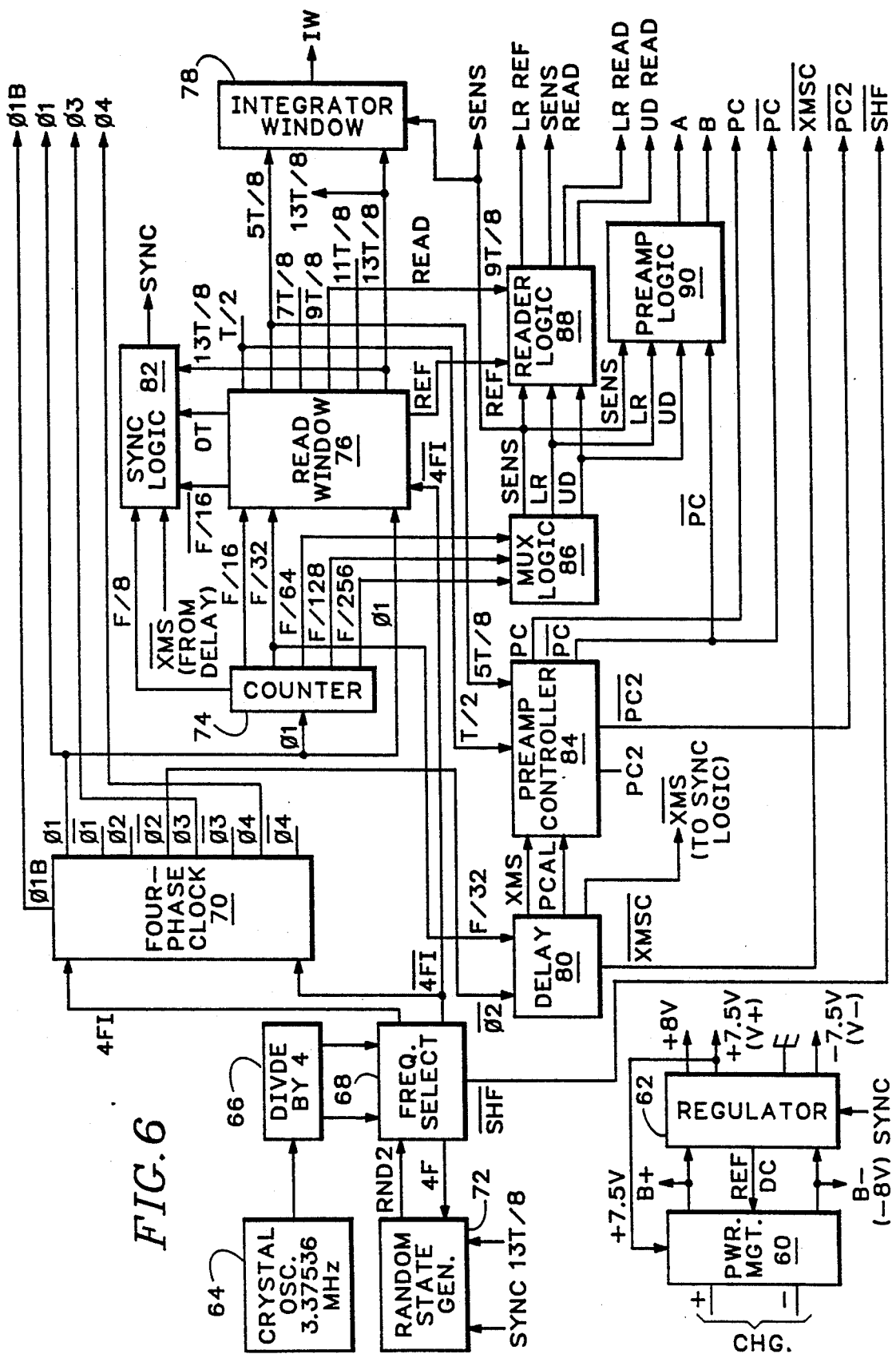
FIG. 6 is a schematic block diagram of the transmit/receive and signal processing circuits housed in the probe of FIG. 1.

A schematic block diagram of the system electronics is shown in FIGS. 6 and 6a. Referring first to FIG. 6, the probe 10 is powered by a power management circuit 60 and a switching voltage regulator 62. Power management is provided by four rechargeable batteries and the regulator, which provides ±8 volts and ±7.5 volts DC is a switching regulator that includes a SYNC input. The purpose of this input is to insure that the regulator 62 is not switching during the "read" windows for the up/down and right/left coils as will be explained below.

Timing is provided by a crystal oscillator 64 which is connected to a divide by four circuit 66. The output of the divide by four circuit 66 is coupled to a frequency select circuit 68 which in turn drives a four phase clock 70. A random state generator 72 is coupled to the frequency select circuit 68 for dithering the frequency select circuit 68 to affect the duty cycle of the frequency select output in a random fashion. The random state generator 72 feeds a pulse RND2 to the frequency select circuit 68 at random times to interrupt the system timing in such a way as to prevent two systems operating in close proximity from being coherent for any length of time. This effectively reduces interference between two adjacent systems by a factor of about 10:1 and allows the systems to operate closer together by a factor of about 3:1.

The frequency select circuit 68 selects one of two operating frequencies for the system in response to the push button located on the front panel as shown in FIG. 1a, depending upon whether the system is to search for the distal target 34 or the proximal target 32. The 4FI and $\overline{4FI}$ signals are provided to a four phase clock 70 which has five outputs, each of which is $\frac{1}{4}$ the frequency of 4FI and $\overline{4FI}$. These outputs of the four phase clock 70 are square waves but differ in phase. These are designated $\phi 1$, $\phi 2$, $\phi 3$, $\phi 4$, and their complements. The frequency of these signals is equal to the frequency that is applied to the transmitter coil. This frequency will be either 211 kHz or 422 kHz. A $\phi 1B$ signal is also applied to the demodulator. This signal is a buffered signal that is required to prevent feedback from the demodulator from affecting the true $\phi 1$ signal.

The four-phase clock 70 is coupled to a counter 74 that develops six frequency divided signals from the $\phi 1$ output of the clock 70. The signals are F/8, F/16, F/32, F/64, F/128, and F/256. These are frequency divided signals that have various purposes as will be explained below. The F/16 and F/32 outputs of the counter 74 are coupled to a read window circuit 76. The purpose of the read window 76 is to develop the positive-going 25% duty cycle 9T/8 or READ pulse which defines the receiver on-time. The read window 76 also develops signals 5T/8 and 13T/8 which are coupled to an integrator window 78 whose function will be explained below. T is the period of the transmitter frequency. All of the delay times are referenced to the F/32 negative-going transition.

The F/32 signal from the counter 74 and the $\phi 2$ signal from the four phase clock 70 are coupled to a delay circuit 80. The delay circuit 80 develops XMS and $\overline{XMS}$. XMS is identical to F/32 except that it is delayed by $\frac{1}{4}$T. This circuit also develops PCAL which is used for certain calibration operations not discussed herein. The principal purpose of the delay circuit 80 is to provide a $\frac{1}{4}$T delay in $\overline{XMSC}$, which is the signal used to turn the coil driver on and off, relative to F/32 in order to make the coil driver (driving in phase with $\phi 1$) start and end the transmitter on-time with $\frac{1}{2}$ cycle periods of a single polarity rather than starting and ending with $\frac{1}{4}$ cycle periods. This helps prevent high peak currents in the transmitter coil (coils 40 and 41) after transmitter turn on, and it helps prevent high residual currents in the transmitter coil system at the end of the transmitter on-time. The reason for this is that the current in the coil, which lags the voltage turn-on or turn-off, will rise to zero or decay to zero during the ¼ cycle positive pulse. This zero current switching feature is very important in order to eliminate current from the transmitter coil during the times that the read windows are opening and the coils 40, 41 are being used as sensing receiver coils.

The read window 76 has outputs F/16 and OT which are connected to sync logic circuit 82. These signals, in conjunction with $\overline{XMS}$ from the delay circuit 80 and F/8 from the counter 74, are used to develop the SYNC signal which forms an input to the regulator 62 and the random state generator 72.

The output of the delay labeled XMS is coupled to the preamp controller which also receives inputs T/2 and 5T/8 to generate the PC and $\overline{PC}$ signals. PC is approximately a square wave with frequency F having a rising edge aligned with the rising edge of T/2 and having a falling edge aligned with the rising edge of XMS. During normal operation the $\overline{PC}$ output is used to control the on-time of the preamp MUX section. The preamp MUX is allowed to be "on" whenever $\overline{PC}$ is low. This means it turns on at the rising edge of T/2 and remains on until the beginning of the transmitter on-time when XMS goes high. The PC and $\overline{PC}$ outputs are both used to control injection of certain compensatory signals into the preamp MUX section when it turns on. The preamp controller 84 also develops $\overline{PC2}$ which has a falling edge aligned with the rising edge of 5T/8. This output is used to control switching in the preamp section.

Three outputs of the counter 74 which are F/64, F/128 and F/256 are coupled to a MUX logic circuit 86. This circuit logically combines these three inputs to develop three positive-going outputs called SENS, LR and UD. One and only one of these outputs is in its high state at any given time. These three outputs define the SENS, LR and UD periods which are the windows for reading signals on the sensing coil 40 and 41, the left/right receiver coils 44a, 44b and the up/down receiver coils 42a, 42b. These three signals are coupled to reader logic circuit 88 and preamp logic circuit 90.

The three outputs of the MUX logic circuit 86 are signals that define eight periods of a system cycle but they do not identify the specific times during each of the eight periods when the receiver should be reading each of three input coil systems. The function of the reader logic circuit is to logically combine SENS, LR and UD with another input, 9T/8, the read pulse to generate SENS READ, LR READ and UD READ which are positive-going pulses that control the receiver. The reader logic section also develops an LR REF output by combining the LR READ input with the REF input. The LR REF output is identical to the REF input except that it occurs only during LR periods. The LR REF output serves as an input to the preamp section where it turns on autozeroing feedback loops.

The preamp logic circuit 90 is connected to the outputs of the MUX logic circuit 86 and the PC output of the preamp controller 84. The function of the preamp logic circuit 90 is to generate a digital code that selects ground potential, the sensing coil 40, 41, the left/right coils 44a, 44b or the up/down coils 42a, 42b, respectively. The particular output code is based upon whichever one of the SENS, LR or UD signals is high unless $\overline{PC}$ is also high. If PC is high, ground potential is selected. Because of the timing of the $\overline{PC}$ signal, ground potential is selected from the time the transmitter turns on until shortly after the transmitter turns off when $\overline{PC}$ is set low by the rising edge of T/2. The read window begins 5T/8 later (refer to FIG. 7) as a result of the 9T/8 pulse from the read window 76. This delay insures a dead zone between transmitter turn-off and the beginning of the read window to allow transients (which can result from nearby metal objects, body tissue conductivity, or electrostatic effects in body tissue) to decay prior to activating the receiver coils. This brief dead zone therefore serves to eliminate a great deal of noise that would otherwise interfere with the reception of signals.

The sync logic section 82 puts out a negative-going SYNC pulse at a frequency of F/32. This pulse controls the regulator 62 in such a way as to guarantee that the output transistor of the regulator 62 is always on (and therefore not switching) during the read period. This prevents switching transients in the regulator from being picked up by the coils and thus causing offsets and noise in the system. (The output transistor is forced "on" rather than "off" because a forced off state results in a regulator duty cycle that is incorrect for achieving the desired amount of voltage step-up.)

The 5T/8 and the 13T/8 pulses developed by the read window 76 are combined by the integrator window 78 to develop a timing pulse IW. The IW pulse activates a feed-back loop in the coil driver circuit 92 that makes fine adjustments in the duty cycle of the transmitter to further eliminate residual current flowing in the transmitter coils during the read period.

Referring now to FIG. 6a the coil driver 92 is the circuit that drives the transmitter coil 40, 41 in a balanced fashion. That is, both ends of the coil are driven, but they are driven to opposite polarities at any given time so that the average potential of the coil always remains near zero. The driver attempts to apply square wave voltages to the two ends of the coil system 40, 41 but the actual voltage applied is somewhat distorted due to interactions of the driver output impedance with the coil current flow and energy storage. The $\phi 1$ input provides the square wave timing.

The $\overline{XMSC}$ input turns the coil driver 92 off when it is high and on when it is low. The timing of $\overline{XMSC}$ relative to $\phi 1$ is such that the coil driver 92 is turned on and off about midway between $\phi 1$ transitions. The delay circuit 80 provides a ¼T delay in $\overline{XMSC}$ relative to F/32 in order to make the coil driver start and end the transmitter on-time with ¼ cycle periods of a single polarity rather than starting and ending with half cycle periods. This helps prevent high peak currents in the transmitter coil near the start of the transmitter on-time and helps prevent high residual currents in the transmitter coil at the end of the transmitter on-time. The coil driver 92 is "on" for 16 $\phi 1$ cycles and then off for 16 $\phi 1$ cycles. When the coil driver 92 is off, the transmitter coil system acts as a sensing coil input to the receiver section. The two ends of the transmitter coil system are connected as input SENSCOIL+ and SENSCOIL− to the preamp MUX circuit 94.

If any residual current flows in the transmitter coil when the coil driver 92 turns off, there will be an exponential decay of the coil voltage that can extend into the read period. If amplified by the preamp section, this voltage can overdrive the preamp and interfere with target readings. A feedback loop operates during the IW pulse which occurs shortly after the coil driver is turned off. The preamp output PO+ is fed back to the coil driver 92 to provide information about the residual current magnitude. This allows the duty cycle of the coil driver to be adjusted in order to set the residual current to a minimum.

The preamp MUX circuit 94 contains a dual four channel multiplexer which responds to a two-line, two-digit code to direct it as to which of four possible differential inputs are to be selected at any given time. Although it is not shown in the drawing of FIG. 6a, the up/down coil system 42a, 42b and right/left coil system 44a, 44b are connected to the preamp MUX circuit 94, along with inputs from the coil driver, SENSCOIL+ and SENSCOIL−. The logic code appears as inputs A and B and represent four possible digital combinations to select either ground, the SENSCOIL inputs and left/right, or up/down. Ground potential is selected during the transmitter on-time and for a short time thereafter (until the T/2 pulse occurs). After this, the appropriate coil selection is made according to the type of period occurring. The readings that are taken appear at the outputs labeled PI+ and PI−.

Switching transients appear in the multiplexer that cause disturbances in the left/right and up/down coil systems. These disturbances cause currents in the coil systems and result in exponential decay voltages. If these voltages are amplified by the preamp, erroneous readings may result. A network (not shown) injects adjustable transients into the coils to counteract the effect of the multiplexer transients. The PC and $\overline{PC}$ inputs to the MUX section 94 act as the source of these counter-transient voltages.

The preamp MUX circuit 94 is connected to a preamp 96 which amplifies the PI+ and PI− inputs by a factor of about 5,000 and develops differential outputs PO+ and PO−. The LR REF input activates feedback loops within the preamp 96 to eliminate offsets that would otherwise cause PO+ and PO− to deviate away from ground potential. The $\overline{PC2}$ input controls switching and is delayed to allow transients to settle so that this circuit does not generate noise during the read window.

The PO+ and PO− outputs of the preamp are applied to a demodulator 98 which is a synchronous demodulator that demodulates the PO+ and PO− inputs by connecting the output DEMOD OUT to PO+ or PO− alternately according to the state of the $\phi 3$ $\phi 1B$ or $\phi 4$ inputs. The decision as to which of the three inputs is to serve as a phase reference or to control the demodulator is based on the states of the SENS and SHF inputs. If the lower of the two system frequencies has been selected, SHF is high and $\phi 3$ controls the demodulator. If the higher frequency is selected, control of the demodulator depends on which period of the system cycle is occurring. If it is an LR or UD period, $\phi 4$ controls, but if it is a SENS period, a high condition on the SENS input dictates that $\phi 1B$ controls. The phase shifts of the coil systems and preamp are greater at the high frequency than at the low frequency. This accounts for the need for two different phase references at the two frequencies. In addition, the phase of the SENS return is sufficiently different from the phase of the LR and UD returns (at the high frequency) that the two different phase references are needed for these cases as well.

The output of the demodulator 98, DEMOD OUT is coupled as an input to SENS reader circuit 100, LR reader circuit 102, and UD reader 104.

The SENS reader 100 reads the information on the DEMOD OUT line only when a timing pulse is present on the SENS read input line. It converts the demodulated target signal information to DC and amplifies it. The amplified DC appears at its output, SENS DC. It removes DC offsets to establish a zero reference so that when no target is being detected SENS DC is essentially at zero. The SENS reader circuit 100 includes a sample and hold circuit with a feedback loop that forces SENS DC to zero whenever the search switch on the front panel is open, essentially keeping the output of the SENS reader 100 in a reset state. When the search switch is closed, the sample and hold circuit changes to its hold state and the feedback loop opens but the sample and hold output remains steady and maintains SENS DC at zero volts until a target is detected. $\overline{SHF}$ is an input to the SENS reader section and changes state according to the system frequency that has been selected. Trimmer resistors (not shown) are used to adjust the sample and hold circuit output to the center of its range and this adjustment can be accomplished independently at the two different frequencies. The SENS reader also has an output labeled $\overline{LOC}$ which changes state according to the search switch position. The purpose of this pulse is to allow a zeroing adjustment to be made in the other reader circuits when the system is in the reset state.

The LR reader circuit 102 is similar to the SENS reader 100 except that it receives information during the LR period. Also, the DC gain of the LR reader is much higher than that of the SENS reader. It receives the $\overline{LOC}$ output of the SENS reader as an input which directs the LR reader 102 to be in either the reset state or the search state. The DC output of the LR reader is denoted LR DC. The UD reader circuit 104 is identical to the LR reader except that it is responsive to UD period target information, because it receives UD READ as an input instead of LR READ. Its output is labeled UD DC.

The outputs of the reader sections 100, 102 and 104 are coupled to a display circuit 106. The display circuit 106 drives the LEDs 22 and 24a, 24b 24c and 24d on the upper face of the search head 12. The three reader inputs SENS DC, LR DC, and UD DC are required in order to determine the correct LED states. The $\overline{LOC}$ signal is also an input to the display circuit 106 and if the $\overline{LOC}$ input is high, indicating that the unit is in its reset state, no LEDs are allowed to be turned on.

SENS DC is zero when no target is present, but when the detection coils approach a target, SENS DC shifts negative. If the amplitude of this negative shift is at least 60 millivolts the display section recognizes that a target is being detected and allows one or more LEDs to turn on according to the voltages present at the LR DC and UD DC inputs. If the target is being detected but it is not centered, one or more of the directional indicator LEDs 24a, 24b, 24c or 24d will turn on depending upon where the target is relative to the up/down or right/left axes. For example, if the target is high and to the left, LEDs 24a and 24d will turn on. If a target is being detected and it is centered on both axes, the four centering LEDs 22 and only these LEDs will be allowed to turn on. The display circuit 106 includes four voltage comparators that operate within a voltage window determined by the amplitude of SENS DC. When the target return signal strength represented by SENS DC produces a voltage that exceeds 60 mv it enables the comparators to turn on the appropriate ones of the four LEDs representing left, right, up or down according to signal strengths and polarities of LR DC and UD DC relative to SENS DC. When the signal strength represented by SENS DC remains high, but LR DC and UD DC are both within the windows set by SENS DC, the target is centered. This disables the up/down and right-/left LEDs and enables the marking window LEDs 22. The windows are set by SENS DC so that they are wider for close range targets and narrower for targets farther away. This makes the centering indicators independent of the distance to the target.

Figure 7:
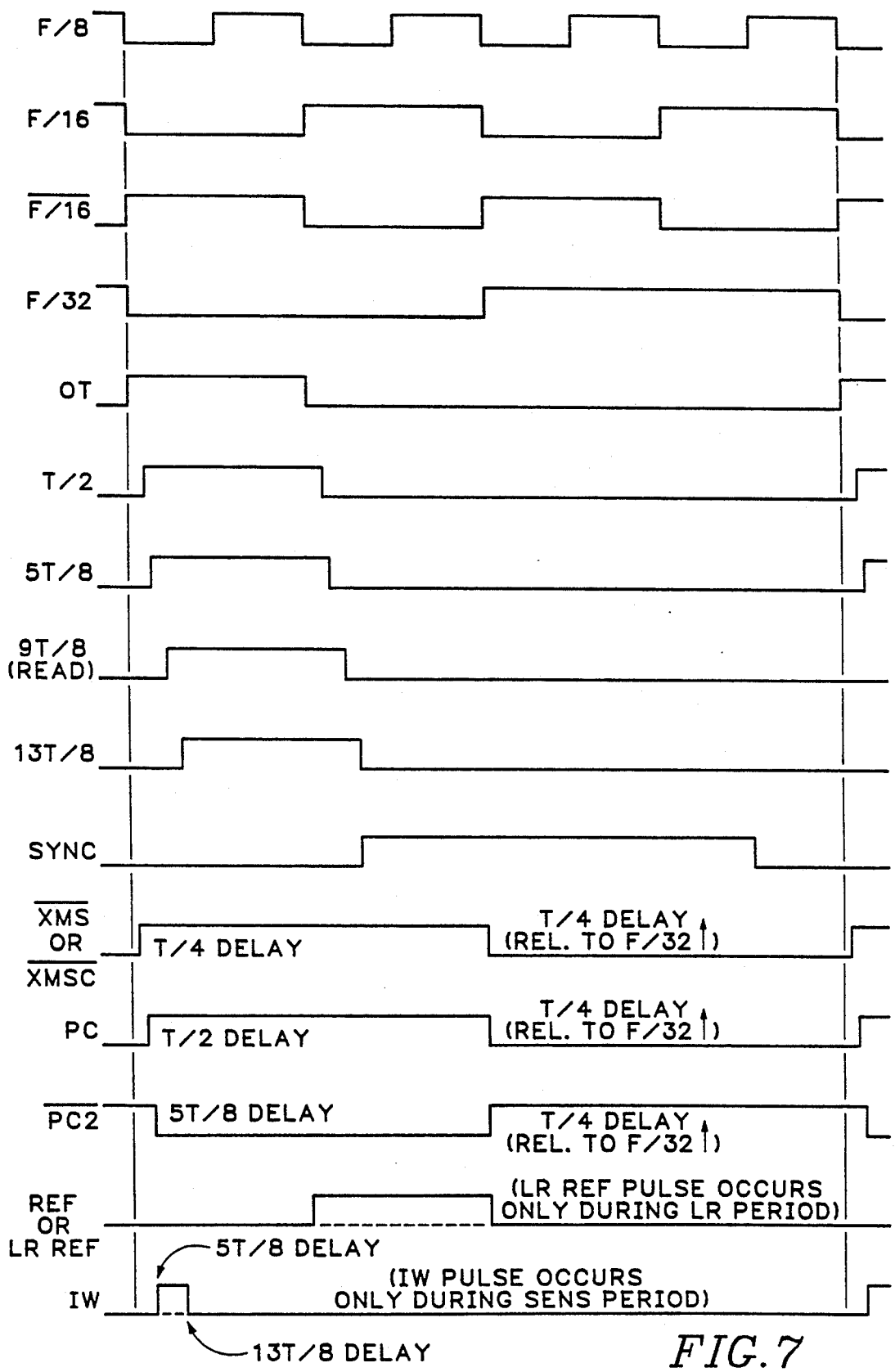
FIG. 7 is a timing waveform diagram showing the transmit/receive cycle of the probe of FIG. 1.
Figure 8:
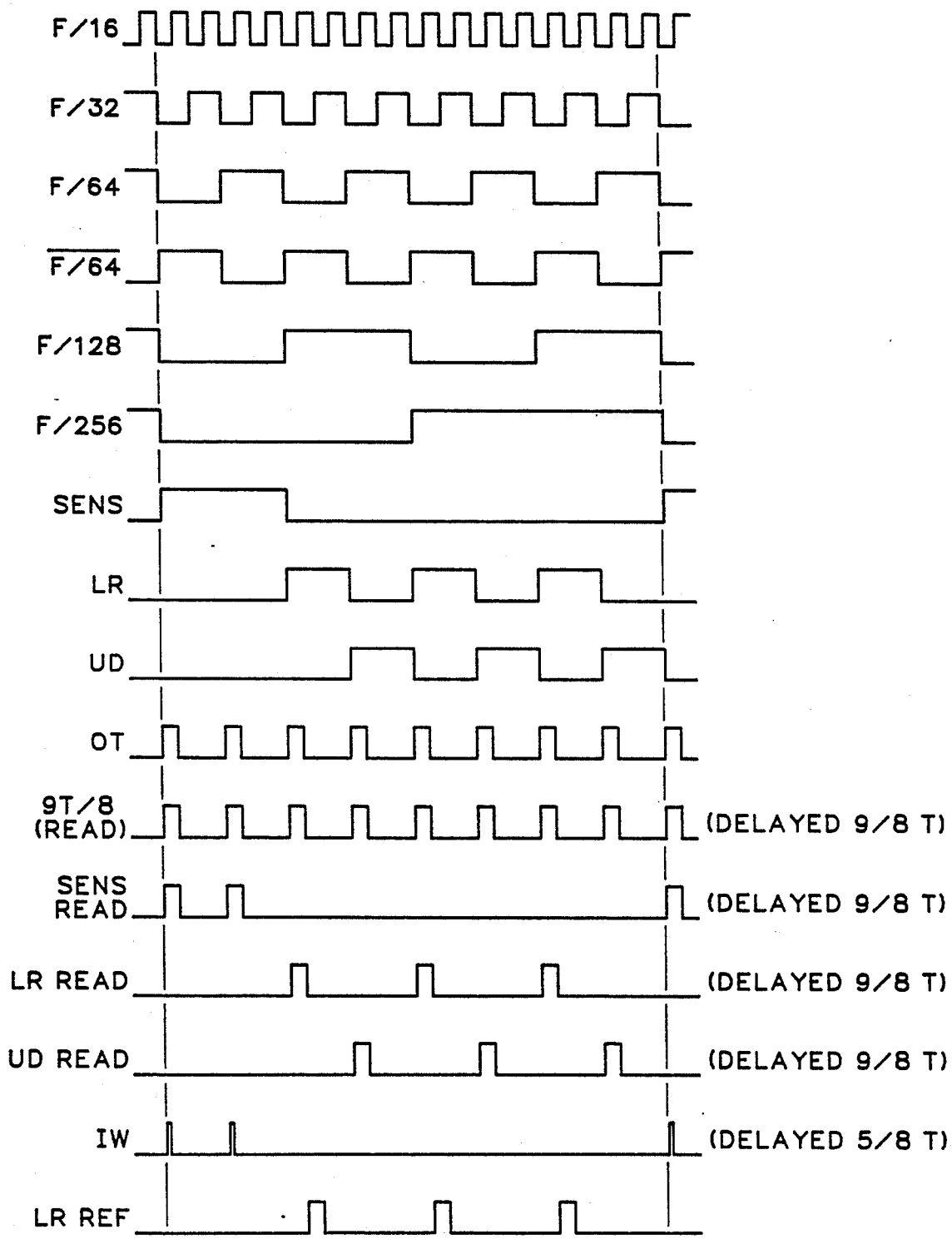
FIG. 8 is a waveform timing diagram showing the system cycle of the probe of FIG. 1.
Figure 9:
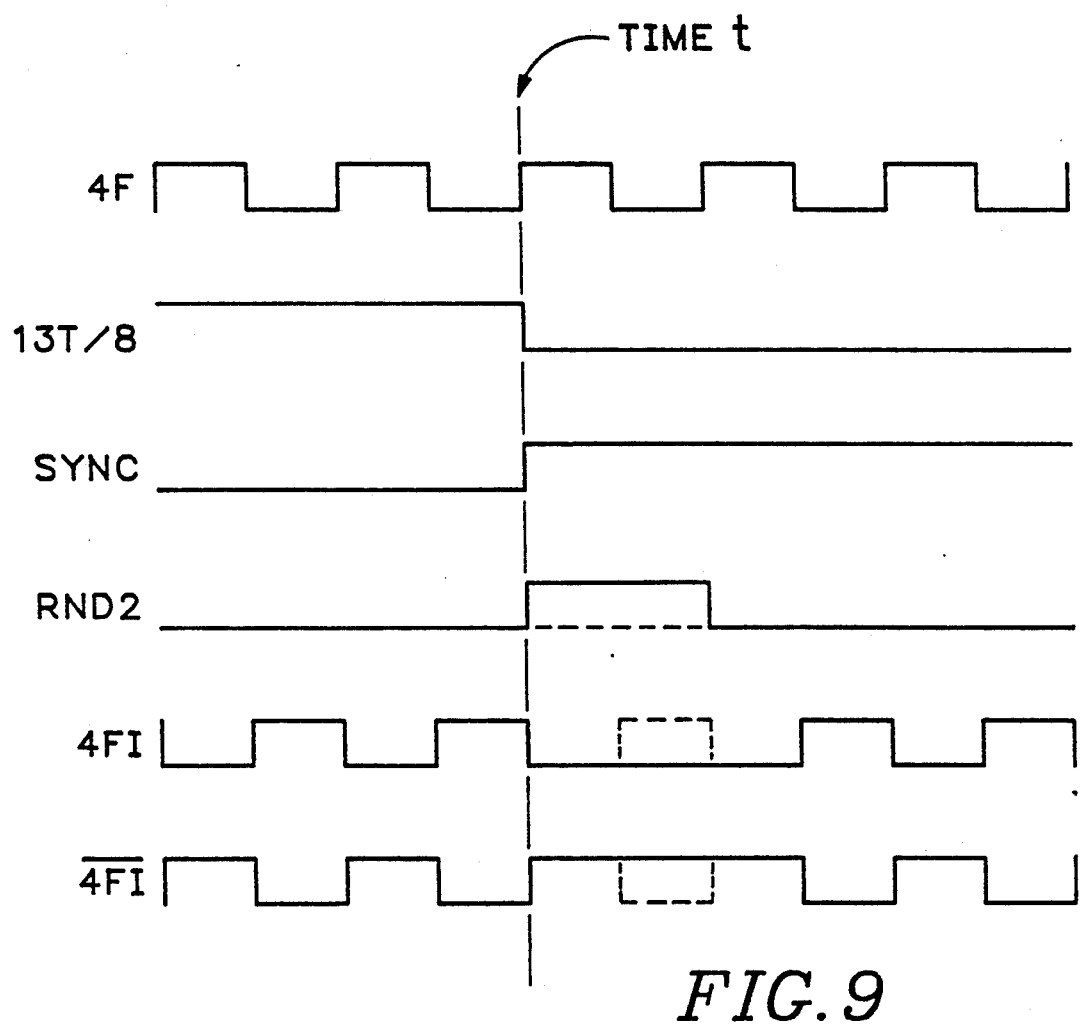
FIG. 9 is a waveform timing diagram illustrating a timing interruption feature of the circuit of FIGS. 6 and 6A.

The relative timing of the waveforms used in the circuits of FIG. 6 and 6a are illustrated in FIGS. 7, 8 and 9. Referring to FIG. 7, a timing diagram is provided for the transmit/receive cycle. Only one of the receiver coils, either the SENS coil, the left/right coil or the up/down coil is read during each transmit/receive cycle. The receiver on-time is set by the 9T/8 positive-going pulse which is an output of the read window 76. The total cycle time of the transmit/receive cycle is 32 $\phi1$ cycles and is equal to the period of the F/32 counter output. The transmitter on-time approximately corresponds with the positive portion of the F/32 square wave. However, there is a quarter $\phi1$ cycle delay in the turn-on and turn-off times of the transmitter which is generated by the delay circuit 80. This is illustrated by the timing of the $\overline{XMSC}$ wave form.

Eight of the transmit/receive cycles occur during one system cycle as illustrated in FIG. 8. During a system cycle the sensing coil is read twice at the beginning of the cycle and the left/right and up/down coils are read three times each in staggered fashion.

FIG. 9 shows the timing diagram for the dithering of the frequency select circuit 68 provided by the random state generator 72. When the random state generator generates a pulse RND2 which is in synchronization with the sync input from SYNC logic circuit 82, the 4FI and $\overline{4FI}$ outputs of the frequency selection circuit 68 have their duty cycles momentarily altered. Since RND2 is generated randomly, two units operating side-by-side or in proximity to one another will not become locked into synchronization with each other and thereby generate noise.

The system has been illustrated using resonant circuit targets wound on a bobbin in three mutually perpendicular axes. For certain applications other targets may work just as well. For example, it may be feasible to print resonant circuits on a thin film which may then be formed into a cylinder. Additionally, the target coils could be configured as loops forming or defining a sphere.

The search head could also be implemented in several other ways. Although the preferred method is to use two D-shaped coils connected series-opposing and having their flat sides adjacent, other receiver coil configurations could be employed. The particular circuitry of the preferred embodiment operates on the theory that a null condition will appear when the target object lies along the axis separating the two D-shaped coils along their flat sides. Since one of the two coil systems is rotated 90° relative to the other, the circuitry can provide information in two axes about which direction the coils must move to center the target. However, it is not necessary that the particular circuitry employed operate to find a null condition in order to provide directional information relative to the target and other types of coil systems in different configurations may be used. For example, in situations in which less directional information is needed, the transmitter and receiver coils may be combined into a single coil system which is multiplexed to the transmit and receive circuits in alternate time windows.

Likewise, it is not necessary that the probe provide visual information about the direction of the target, as audible indicators could also be used. Even if visual indicators are chosen, it is not necessary that such visual indicators be located on the probe itself. The probe may exist quite apart from the display indicators which may be housed at a remote location.

While the present invention has been described as being particularly useful in the field of medical instrumentation, it is not limited to such fields. The invention could be used to determine the location of a target within any body of material or mass. Such material need not be limited to biological tissue. For example, targets could be buried underground or could be embedded in some raw material subject to a process control system. Thus, as the term "body" is used herein, it is understood that this term refers to any body of material or mass containing a target.

Although the resonant circuit targets have been described herein as comprising a coil and a tiny capacitor, the targets could also be constructed as a single coil wire with the parasitic capacitance of the coil acting as the capacitor. Especially at higher frequencies, this target could resonate without the physical addition of a capacitor. Furthermore, although three coils have been shown mounted on a bobbin as a preferred embodiment, the target could be constructed by using less than or even more than three resonant circuits. Three resonant circuits provides the highest degree of accuracy, however, there may be applications where a single resonant circuit will suffice.

The terms and expressions which have been employed in the foregoing specification are used therein as terms of description and not of limitation, and there is no intention, in the use of such terms and expressions, of excluding equivalents of the features shown and described or portions thereof, it being recognized that the scope of the invention is defined and limited on by the claims which follow.

What is claimed is:

1. A system for detecting the position of an object located within a body of material or a mass, comprising;
   (a) at least one resonant circuit, having a resonant frequency, attached to said object;
   (b) transmitter means adapted to be located outside the body for transmitting inductive energy;
   (c) receiver means in operative association with said transmitter means for detecting the ringing of the resonant circuit in response to said inductive energy;
   (d) a probe adapted to be positioned outside the body including at least one transmitting coil and first and second receiver coils, said first receiver coil providing signals indicative of the position of said object relative to a first axis and said second receiver coil providing signals indicative of the position of said object relative to a second axis, said first and second axes being substantially mutually orthogonal, said probe further including a sensing coil for providing a signal indicative of the relative proximity of the object to the receiver means, wherein said first ad second receiver coils each include a pair of coils situated side-by-side in the same plane and connected in series-opposed fashion.

2. The system of claim 1 wherein each pair of receiver coils includes two D-shaped coils with their respective flat peripheries lying adjacent to one another.

3. The system of claim 2 wherein said sensing coil includes at least one substantially circular coil encircling said first and second receiver coils and disposed in substantially the same lane as at least one of said first and second receiver coils.

4. The system of claim 3 wherein said sensing coil comprises a pair of coils connected in series-aiding fashion, one of said pairs of coils being coplanar with said first receiver coil and the other of said pair of coils being coplanar with said second receiver coil.

5. The system of claim 4, further including switching means for periodically coupling a transmitter circuit to said sensing coil for transmitting said inductive energy.

6. The system of claim 1, wherein said resonant circuit includes at least two coils lying in planes mutually perpendicular to one another.

7. The system of claim 6 wherein said resonant circuit is mounted on a bobbin for supporting said two coils and further includes a solenoid coil wound about said two coils.

8. A system for detecting the position of an object located within a body of material or a mass, comprising
(a) at least one resonant circuit, having a resonant frequency, attached to said object;
(b) transmitter means adapted to be located outside the body for transmitting inductive energy;
(c) receiver means in operative association with said transmitter means for detecting the ringing of the resonant circuit in response to said inductive energy;
(d) a probe adapted to be positioned outside the body containing said transmitter means and said receiver means, further including switching means for energizing said transmitter means for a first predetermined period of time and said receiver means for a second predetermined period of time; and
(e) display means for indicating the location of the probe relative to said object.

9. The system of claim 8, further including delay circuit means for delaying the time when said receiver is energized until after said transmitter means is turned off.

10. A system for detecting the position of an object located within a body of material or a mass, comprising:
(a) at least one resonant circuit, having a resonant frequency attached to said object;
(b) transmitter means adapted to be located outside the body for transmitting inductive energy;
(c) receiver means in operative association with said transmitter means for detecting the ringing of the resonant circuit in response to said inductive energy;
(d) a movable probe coupled to said receiver means having a first visual display for indicating the direction that the probe should be moved to center it over the object, wherein said movable probe includes a second visual display for indicating when the probe is centered on the object.

11. The system of claim 10 wherein said probe includes a substantially planar search head supporting said first and second visual displays.

12. The system of claim 11 wherein said first visual display is positioned about an outer periphery of said search head and said second visual display is positioned on said search head to define a target marking window.

13. A system for detecting the position of an object located within a body of material or a mass, comprising:
(a) at least one resonant circuit, having a resonant frequency, attached to said object;
(b) transmitter means adapted to be located outside the body for transmitting inductive energy;
(c) receiver means in operative association with said transmitter means for detecting the ringing of the resonant circuit in response to said inductive energy;
(d) a probe adapted to be positioned outside the body including at least one transmitting coil and first and second receiver coils, said first coil providing signals indicative of the position of said object relative to a first axis and said second coil providing signals of the position of said object relative to a second axis, said first and second axes being substantially mutually orthogonal, said probe further including a sensing coil for providing a signal indicative of the relative proximity of the object to the receiver means, said receiver means including read circuit means for periodically sampling signals present on said sensing coil and on said first and second receiver coils over discrete time frames.

14. A system for detecting the position of an object within a body or mass comprising:
(a) a tube adapted to be inserted into said body containing said object at approximately a first end thereof;
(b) a search head for scanning an outside surface of said body and having a first indicator associated therewith for indicating the direction that the search head should be moved to center it over the object wherein said object means contains resonant circuit means for ringing in response to electromagnetic energy transmitted by said search head, and wherein sad object comprises two targets, each having a resonant circuit with a different resonant frequency.

15. The system of claim 14 wherein said search head includes switch means for selecting either of said resonant frequencies.

16. The system of claim 15 wherein sad resonant frequencies comprise first and second resonant frequencies and said first resonant frequency is an even multiple of said second resonant frequency.

17. The system of claim 14, further including a second indicator associated with the search head for indicating when the search head is centered on the object.

18. The system of clam 17 herein said first and second indicators are located on the search head and provide a visual display.

19. A system for detecting the position of an object located within a body of material or a mass comprising:
(a) at least one resonant circuit having a resonant frequency attached to said object;
(b) transmitter means adapted to be located outside the body for transmitting inductive energy;
(c) receiver means in operative association with said transmitter means for detecting the ringing of the resonant circuit in response to said inductive energy; and (d) a movable probe having a first user perceptible display means for indicating the direction the probe should be moved to center it over the object.

20. The system of claim 19 wherein said receiver means includes a first pair of receiver coils connected in series-opposed fashion.

21. The system of claim 20 further including a second pair of receiver coils connected in series opposed fashion.

22. The system of claim 19 wherein the resonant circuit is incorporated in a tube.

23. The system of claim 22 further including a second resonant circuit incorporated in the tube and spaced apart from the resonant circuit, each of the resonant circuits having a different resonant frequency.

* * * * *

UNITED STATES PATENT AND TRADEMARK OFFICE
CERTIFICATE OF CORRECTION

PATENT NO. : 5,325,873

DATED : July 5, 1994

INVENTOR(S) : James P. Karbowski, et al.

It is certified that error appears in the above-indentified patent and that said Letters Patent is hereby corrected as shown below:

Column 6, line 52, after "D", insert --,--.

Column 7, line 44, after 12, insert --.--.

Column 8, line 60, delete the first occurrence of the word "XMS" and insert

-- $\overline{XMS}$ --.

Column 10, line 3, delete "If PC is high" and insert

--if $\overline{PC}$ is high--.

Column 11, line 34, delete second occurrence of "PC" and insert

--$\overline{PC}$--;

Column 11, line 50, after "$\phi 3$" insert --,--.

Column 12, line 45, after 24b insert --,--.

Column 13, line 2, delete "60 my" and insert --60 mv--.

Column 15, line 12, delete "lane" and insert --plane--.

UNITED STATES PATENT AND TRADEMARK OFFICE
CERTIFICATE OF CORRECTION

PATENT NO. : 5,325,873

DATED : July 5, 1994

INVENTOR(S) : James P. Karbowski, et al.

It is certified that error appears in the above-indentified patent and that said Letters Patent is hereby corrected as shown below:

```
Column 16, line 42, delete "sad" and insert --said--;
Column 16, line 53, delete "sad" and insert --said--; and
Column 16, line 56, delete "clam 17" and insert
--claim 17--;
Column 16, line 56, delete "herein" and insert
--wherein--.
```

Signed and Sealed this

Thirteenth Day of June, 1995

Attest:

BRUCE LEHMAN

Attesting Officer

Commissioner of Patents and Trademarks